US005426704A

United States Patent [19]

Tamamura et al.

[11] Patent Number: 5,426,704

[45] Date of Patent: Jun. 20, 1995

[54] NOISE REDUCING APPARATUS

[75] Inventors: Manpei Tamamura; Eiji Shibata; Hiroshi Iidaka, all of Tokyo; Manabu Nohara, Saitama, all of Japan

[73] Assignee: Pioneer Electronic Corporation, Tokyo, Japan

[21] Appl. No.: 94,449

[22] Filed: Jul. 21, 1993

[30] Foreign Application Priority Data

Jul. 22, 1992 [JP] Japan .............................. 4-195462
Aug. 13, 1992 [JP] Japan .............................. 4-215830

[51] Int. Cl.[6] .............................. A61F 11/06
[52] U.S. Cl. .............................. 381/71
[58] Field of Search .............................. 381/71, 94, 86; 364/724.2, 724.01, 724.19

[56] References Cited

U.S. PATENT DOCUMENTS 4,677,676 6/1987 Erikkson .............................. 381/71
5,022,082 6/1991 Erikkson et al. .............................. 381/71
5,146,505 9/1992 Pfaff et al. .............................. 381/71
5,245,561 9/1993 Sugiyama .............................. 364/724.2

FOREIGN PATENT DOCUMENTS 3178846 8/1991 Japan .

OTHER PUBLICATIONS

English language abstract for Japanese Patent Application No. 3-178846.

*Primary Examiner*—Curtis Kuntz
*Assistant Examiner*—Ping W. Lee
*Attorney, Agent, or Firm*—Sughrue, Mion, Zinn, Macpeak & Seas

[57] ABSTRACT

A noise reducing apparatus which is particularly effective to reduce periodic noise with the construction simplified very much is disclosed. The noise reducing apparatus comprises a microphone, an adaptive filter for generating a signal to reduce noise inputted to the microphone, transfer characteristic compensation means for generating a signal to compensate for a transfer characteristic when the signal generated from the adaptive filter comes the microphone, a synchronizing pulse generation circuit for generating a pulse signal synchronized with the period of the noise, a pulse interval detection circuit for detecting the interval between pulses of the pulse signal, tap number changeover means for changing over the number of taps of the adaptive filter to a number with which the delay amount of a tapped delay line of the adaptive filter is equal to the interval detected by the pulse interval detection circuit, and a loudspeaker for generating sounds in response to the signal from the adaptive filter. Also a noise reducing apparatus suitable for with an automobile.

3 Claims, 11 Drawing Sheets

FIG. 5

$W_0$ , $W_1$ , • • • • • , $W_{K-2}$ , • • , $W_K$ , • • • • • , $W_I$

OUTPUT y(n) IS SUM OF COEFFICIENTS IN THIS SECTION

FIG. 6

$W_0$ , $W_1$ , • • • • • , $W_{K-J}$ , • • , $W_K$ , • • • • • , $W_I$

UPDATE COEFFICIENTS ONLY IN THIS SECTION

NOISE REDUCING APPARATUS

BACKGROUND OF THE INVENTION

1. Field of the Invention

This invention relates to a noise reducing apparatus of the type which reduces noise by generating a signal which is equal in amplitude but reverse in phase to the noise to reduce the noise, and more particularly to a noise reducing apparatus of the type mentioned which is suitably used for reduction of periodical noise and also to a noise reducing apparatus which reduces noise in a room of an automobile.

2. Description of the Prior Art

In a room of an automobile, noise is generated by rotation of an engine, and in an air conditioning system, noise is generated by rotation of a fan or a compressor. Such noise often causes people there to have a disagreeable feeling.

One of methods of reducing such noise is disclosed, for example, in Japanese Patent Laid-Open Application No. Heisel 1-178846 wherein s signal which is equal In amplitude but reverse in phase to noise is generated using an adaptive filter to cancel the noise.

An exemplary one of conventional noise reducing apparatus of the type just described is shown in FIG. 9. Referring to FIG. 9, the noise reducing apparatus includes a pickup circuit 11 for picking up noise from a noise source 10, a pair of analog to digital converters (A/D) 12 and 16, a digital to analog converter (D/A) 13, a loudspeaker 14, an adaptive filter 7, a transfer characteristic compensation section 8, and a tap value updating section 9 for updating tap values of the adaptive filter 9.

A microphone 15 is installed at a location where it is desired to reduce noise.

The adaptive filter 7 corrects a signal picked up by the pickup circuit 11 for those portions which are different from noise which is generated from the noise source 10 and inputted to the microphone 15 so that a signal issued from the loudspeaker 14 and coming to the microphone 15 may be equal in amplitude but reverse in phase to the noise from the noise source 10.

The adaptive filter 7 is constituted from a digital filter formed from a tapped delay line as described in detail below with reference to FIG. 10. In particular, the adaptive filter 7 can transform a signal of any waveform by the Fourier transform to decompose the signal into a frequency spectrum. Further, if the frequency spectrum is the same, then a same waveform can be obtained by the Fourier transform. Accordingly, the adaptive filter 7 controls a passing spectrum so that the spectrum of a signal picked up by the pickup circuit 11 may be the same as the spectrum of a noise signal from the noise source 10 received by the microphone 15.

The tap value updating section 9 updates the tap values of the adaptive filter 7 to make a filter characteristic so that the passing spectrum may be the same as the spectrum of the noise signal.

The transfer characteristic compensation section generates a compensation signal to compensate, since a signal generated by the adaptive filter 7 is influenced by a time delay and a frequency band limitation before it comes to the microphone 15 by way of the digital to analog converter 13 and the loudspeaker 14, for the transfer characteristic so that the signal at the input to the microphone 15 may be equal in amplitude but reverse in phase to the signal from the noise source 10.

Also the transfer characteristic compensation section 8 may be constructed from a digital filter formed from a tapped delay line. A detailed construction of the transfer characteristic compensation section 8 is shown in FIG. 11. Referring to FIG. 11, the transfer characteristic compensation section 8 shown includes a plurality of delay elements 80-1 to 80-J each of which delays an input signal by a time equal to a sampling interval of sampling pulses inputted to the analog to digital converters 12 and 16. An output value of each of the delay elements 80-1 to 80-J is multiplied by a tap value by a corresponding one of tap value multipliers 81-0 to 81-J.

Thus, where the output value of the analog to digital converter 12 when $t=t_n$ tn is represented by x(n) and the output value subsequently when $t=t_{n+1}$ is represented by x(n+1) and besides a sum $$\sum_{i=1}^{3} x_i \text{ is represented by } \sum_{i=1}^{3} x_i = x_1 + x_2 + x_3$$

a compensation signal C(n) from the transfer characteristic compensation section 8 outputted from an adder 82 is given by $$C(n) = \sum_{i=0}^{J} x(n-1)Ci \tag{1}$$

Referring now to FIG. 10, the adaptive filter 7 includes delay elements 70-1 to 70-Z, tap value circuits 71-0 to 71-Z and an adder 72. The delay elements 70-1 to 70-Z successively delay an output signal of the analog to digital converter 12 each by a time equal to the production interval of sampling pulses.

Accordingly, the output y(n) of the adaptive filter 7 is given by $$y(n) = \sum_{i=0}^{Z} x(n-1)Wi(n) \tag{2}$$

and the output (y) is converted into an analog signal by the digital to analog converter 13 (FIG. 7) and then sent out from the loudspeaker 14.

The tap values $W_0$ (n) to $W_z$ (n) of the adaptive filter 7 are updated each time a sampling pulse is generated. Such updating of the tap values is performed by the tap value updating section 9.

The tap value updating section 9 includes three stages of multipliers 90. 91 and 92 and a stage of adders 93.

An output signal C(n) of the transfer characteristic compensation section 8 is successively inputted to the delay elements 90-1 to 90-Z. by each of which it is delayed by a time equal to the production interval of sampling pulses.

Meanwhile, the multiplier 91 multiplies, by $\alpha$, a signal e(n) obtained by conversion of an output e(t) of the microphone 15 into a digital value by the analog to digital converter 16. The value g is determined depending upon the loop characteristic of the adaptive control system.

The tap value updating section 9 then performs calculation of updated values W(n+1) of the tap values of the adaptive filter 7. In order to facilitate description, updating of the tap value $W_0$ (n) of the tap 71-0 to Wo (n+1) will be described as an example.

At the multiplier 92-0, multiplication between an output of the multiplier 91 and an output value C(n) from the transfer characteristic compensation section 8 is performed. The adder 93-0 subtracts an output value of the multiplier 92-0 from the tap value $W_0$ (n) at a sampling time of $t=t_n$ and updates the tap value with a result of the subtraction as a tap value $W_0$ (n+1) at a next sampling time of $t=t_{n+1}$. In particular, updating of the tap value given by $$W_0(n+1)=W_0(n)-\alpha\, C(n)\, e(n) \quad \ldots (3)$$

is performed. Further, also for any other tap $W_i$, updating of the tap value given by $$W_1(n+1)=W_i(n)-\alpha\, C(n-1)\, e(n) \quad \ldots (4)$$

is performed.

Since the tap values are updated in such a manner as described above, sound waves sent out from the loudspeaker 14 are equal in amplitude but reverse in phase to noise from the noise source 10 at the input of the microphone 15, and consequently, noise in the proximity of the microphone 15 is cancelled or reduced.

As described above, the conventional noise reducing apparatus is constructed such that a noise signal picked up from a noise source is passed through an adaptive filter to generate a signal which is equal in amplitude but reverse in phase to the noise to reduce the noise.

To this end, the adaptive filter must perform a number of multiplications equal to the number of taps, and a number of multiplications and additions equal to the number of taps are required for updating of the tap values.

If the multiplications and the additions are performed with individual multipliers and adders constructed therefor, the construction of the apparatus is complicated very much, and therefore, they are normally performed by processing by means of a processor. However, a high speed processor is required in order for processing of multiplications and additions corresponding to a very great number of taps as described above to be performed within a time of an interval between sampling pulses, and this makes the cost of the apparatus high.

FIG. 12 shows an exemplary one of conventional noise reducing apparatus of the type described above which is specifically applied to reduce noise in a room of an automobile. Referring to FIG. 12, the noise reducing apparatus shown includes a microphone 101 installed at a location where it is desired to reduce noise, a noise signal pickup 104 for picking up a noise signal, an adaptive filter 105, and a loudspeaker 108.

The adaptive filter 105 corrects a signal picked up by the noise signal pickup 104 for portions which are different from noise inputted to the microphone 101 so that a signal developed from the loudspeaker 108 in accordance with the corrected signal and coming to the microphone 101 may be equal in amplitude but reverse in phase to the noise.

When the signal corrected by the adaptive filter 105 and developed from the loudspeaker 108 is, at the location where the microphone 101 is disposed, not a signal which is equal in amplitude but reverse in phase to the noise, a signal corresponding to a difference between the signal and the noise appears in the output of the microphone 101 and fed back to the adaptive filter 105.

The adaptive filter 105 is constituted from a digital filter formed from a tapped delay line not shown, and a transfer characteristic compensation section not shown.

As described above, a signal of any waveform can be decomposed into a frequency spectrum by the Fourier transform of the same. Further, if the frequency spectrum is the same, then the same waveform can be obtained by the inverse Fourier transform. Accordingly, the tap values of the digital filter are varied in response to a feedback signal from the microphone 101 to make a filter characteristic so that the same spectrum as the spectrum of noise may be obtained.

Meanwhile, the transfer characteristic compensation section compensates for an influence of a time delay and a frequency band limitation while a signal generated by the digital filter comes to the microphone 101 so that a signal equal in amplitude but reverse in phase to the noise may be obtained at the input to the microphone 101.

In this manner, the conventional noise reducing apparatus for an automobile is constituted from the microphone 101, the noise pickup 104, the adaptive filter 105 and the loudspeaker 108.

The loudspeaker 108 develops a signal having the same spectrum as the noise. Since the frequency spectrum of such noise includes noise components from a low frequency component to a high frequency component, in order for low frequency components to be developed efficiently, the loudspeaker must be sufficiently large.

Therefore, the loudspeaker is installed, for example, below a seat of an automobile as seen in FIG. 12 also taking the good appearance of the room of the automobile into consideration.

On the other hand, the microphone 101 is installed at a location where noise is desired to be reduced. In particular, the microphone 101 is installed at a location near the ears of a driver or a passenger of the automobile such as, for example, on the ceiling above the seat as seen in FIG. 12.

Where the loudspeaker and the microphone are installed in a spaced relationship from each other in this manner, the noise reducing effect is high for noise of low frequencies, but is as low as zero for noise of high frequencies as seen from FIG. 13.

It is considered that this arises from the fact that, when sound waves propagate in a closed space of a room of a vehicle, the transfer characteristic is fluctuated by such a cause that sound waves of a high frequency propagate with a greater number of reflections than sound waves of a low frequency. In other words, it is considered that the transfer characteristic set to the adaptive filter and the actual transfer characteristic are made different from each other for a high frequency signal by the variation in ratio at which the driver and/or passenger or passengers occupy in the space (whether they are fat or slim) and the variation of the sitting positions of them.

SUMMARY OF THE INVENTION

It is an object of the present invention to provide a noise reducing apparatus which is particularly effective to reduce periodic noise with the construction simplified very much.

It is another object of the present invention to provide a noise reducing apparatus for a room of an automobile which assures a high noise reducing effect also for noise of high frequencies.

In the conventional noise reducing apparatus described hereinabove with reference to FIGS. 9 to 11, a signal picked up from a noise source is inputted to the adaptive filter as a signal proximate to the spectrum of the noise inputted to the microphone.

However, the signal to be inputted to the adaptive filter need not be a signal proximate to the spectrum of the noise but may be any signal only if it has a spectrum which includes the spectrum of the noise. In other words, if the spectrum of the noise is included in the signal, then the spectrum characteristic of the signal can be adjusted to the spectrum of the noise by varying the characteristic of the filter so that a waveform the same as the waveform of the noise can be obtained.

Further, for periodic noise, the filter characteristic can be obtained also by setting the total delay amount of a tapped delay line constituting the adaptive filter to a time equal to the period of the noise. In particular, since the noise is periodic, a response to the noise signal for one period is divided by the period of the noise, and the principle of superposition wherein the response divisions are superimposed stands. This is equivalent to the fact that the delay amount of the tapped delay line is divided by a time equal to the period of the noise and the delay amount divisions are superimposed to obtain a superimposed tap value, which is set as a tap value.

The present invention is based on this principle, and while the calculation processing of the adaptive filter in the conventional noise reducing apparatus is performed to calculate y(n) for i=0 to Z in accordance with the equation (2) given hereinabove, the calculation processing in the noise reducing apparatus of the present invention is performed for those taps up to the Ith tap by which a delay amount equal to the period of the noise is provided. Further, since the calculation processing for those taps up to the Ith tap is performed by the adaptive filter. updating of tap values is required only for i=0 to I of $W_i$ given by the equation (4) given hereinabove.

Further, where a pulse signal synchronized with the period of the noise generated from the noise source is inputted as an input signal to the adaptive filter. since the spectrum of the pulse signal is very wide, the pulse signal includes the spectrum of the noise.

Further, if the amplitude x of the pulse signal is normalized with "1", then the equation (2) given hereinabove is rewritten as $$y(n) = \sum_{i=K_1}^{K_2} W_i(n) \quad (5)$$

where $K_1$ and $K_2$ are orderly numbers of delay elements at which a pulse is present, and for $i=K_1$ to $K_2$ represents that a pulse is present in those delay elements from the $K_1$th to the $K_2$th delay elements both inclusive. As can be seen from the equation (5) above, the calculation processing of the adaptive filter is simplified so that it only includes additions.

Thus, in order to attain the objects described above, according to an aspect of the present invention, there is provided a noise reducing apparatus, which comprises a microphone, an adaptive filter for generating a signal to reduce noise inputted to the microphone, transfer characteristic compensation means for generating a signal to compensate for a transfer characteristic when the signal generated from the adaptive filter in response to an output of the microphone comes the microphone, a synchronizing pulse generation circuit for generating a pulse signal synchronized with the period of the noise, a pulse interval detection circuit for detecting the interval between pulses of the pulse signal generated from the synchronizing pulse generation circuit, tap number change-over means for changing over the number of taps of the adaptive filter to a number with which the delay amount of a tapped, delay line of the adaptive filter is equal to the interval detected by the pulse interval detection circuit, and a loudspeaker for generating sounds in response to the signal from the adaptive filter.

In the noise reducing apparatus, the synchronization pulse generation circuit generates a pulse signal synchronized with the period of the noise and inputs the pulse signal to the adaptive filter and the transfer characteristic compensation means detects the interval of pulses generated from the synchronization pulse generation circuit. The tap number change-over means changes over the tap number to close it at which the delay amount of the tapped delay line of the adaptive filter is equal to the distance of pulses detected by the pulse interval detection circuit.

Since a pulse signal synchronized with the period of noise is generated and inputted to the adaptive filter and the number of taps of the tapped delay line of the adaptive filter is closed with a number of taps by which a delay amount equal to the interval of pulses of the inputted pulse signal is obtained, the number of operations in calculation processing of the adaptive filter can be reduced remarkably, and the apparatus can be constructed in a simplified construction.

Preferably, the transfer characteristic compensation means includes a non-volatile memory in which tap values are stored in advance and generates a signal for compensation for the transfer characteristic in synchronism with the pulse signal from the synchronizing pulse generation circuit. Since the tape values are stored in advance in the non-volatile memory, they can be obtained readily without conducting calculation processing for them.

According to another aspect of the present invention, there is provided a noise reducing apparatus for a room of an automobile, which comprises a microphone, an adaptive filter for generating a signal equal in amplitude but reverse in phase to noise inputted to the microphone to reduce the noise in the room of the automobile, a microphone installed on a ceiling above a seat of the automobile for outputting a control signal to the adaptive filter, a low frequency band loudspeaker installed below the seat for receiving the signal from the adaptive filter and generating noise of a low frequency portion of the received signal, and a high frequency band loudspeaker installed on the ceiling above the seat for receiving the signal from the adaptive filter and generating noise of a high frequency portion of the received signal.

In the noise reducing apparatus for a room of an automobile, the microphone for outputting a control signal to the adaptive filter is installed, as a location where it is desired to reduce noise, on the ceiling of the automobile near the ears of the driver and/or a passenger or passengers above the seat. Further, the low frequency band loudspeaker for sending out a signal of a low frequency band from the adaptive filter is installed below the seat. Meanwhile, the high frequency band loudspeaker for sending out a signal of a high frequency band from the adaptive filter is installed on the ceiling above the seat.

Since the high frequency band loudspeaker is small in size, even if it is installed on the ceiling above the seat, the distance thereof to the microphone can be made small without impairing the good appearance of the room of the automobile. As a result, the level of main waves of a signal of a high frequency band is very high comparing with the level of reflection waves, and consequently, the fluctuation of the transfer characteristic is reduced and a high noise reducing effect is assured in the high frequency band.

Thus, since the low frequency band loudspeaker and the high frequency band loudspeaker for sending out portions of the signal from the adaptive filter in the low frequency band and the high frequency band separately from each other are provided and the former is installed below the seat while the latter is installed on the ceiling in the neighborhood of the microphone above the seat, not only noise in the low frequency band but also noise in the high frequency band can be reduced efficiently.

The above and other objects, features and advantages of the present invention will become apparent from the following description and the appended claims, taken in conjunction with the accompanying drawings in which like parts or elements are denoted by like reference characters.

BRIEF DESCRIPTION OF THE DRAWINGS

FIG. 5 is a diagrammatic view illustrating calculation of an output value of the adaptive filter;

FIG. 6 is a similar view but illustrating updating of a tap value of the adaptive filter:

DESCRIPTION OF THE PREFERRED EMBODIMENTS

Figure 1:
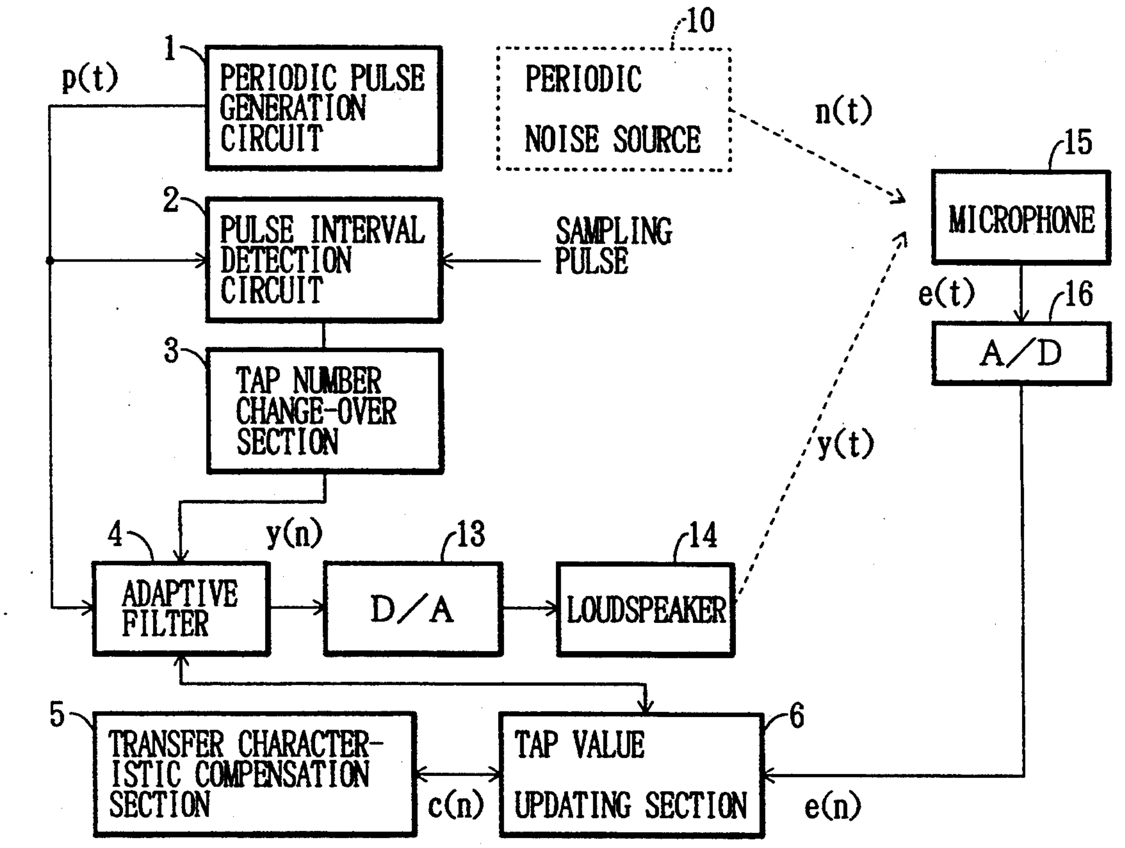
FIG. 1 is a block diagram of a noise reducing apparatus showing a preferred embodiment of the present invention.

Referring first to FIG. 1, there is shown a general construction of a noise reducing apparatus to which the present invention is applied. The noise reducing apparatus shown includes a synchronizing pulse generation circuit 1 which generates pulses synchronized with the period of noise of a noise source 10.

A pulse interval detection circuit 2 detects the interval of pulses generated by the synchronizing pulse generation circuit 1. In the noise reducing apparatus shown, the pulse interval detection circuit 2 detects the interval of pulses with a number of sampling pulses to an analog to digital converter (A/D) 16.

A tap number change-over section 8 changes over the number of taps of an adaptive filter 4 so that it may be equal to the sampling pulse number detected by the pulse interval detection circuit 2.

The noise reducing apparatus further includes a transfer characteristic compensation section 5, a tap value updating section 6, a digital to analog converter (D/A) 13, a loudspeaker 14, a microphone 15 and an analog to digital converter (A/D) 16.

The cycle frequency of sampling pulses is greater than twice the maximum frequency included in a signal outputted from the microphone 15 and is set in advance upon designing of the apparatus.

In order to facilitate description below, it is assumed that the width of a synchronizing pulse p(t) generated from the synchronizing pulse generation circuit 1 is equal to three sampling pulse times, and the pulse interval detected by the pulse interval detection circuit 2 is equal to I sampling periods.

Figure 11:
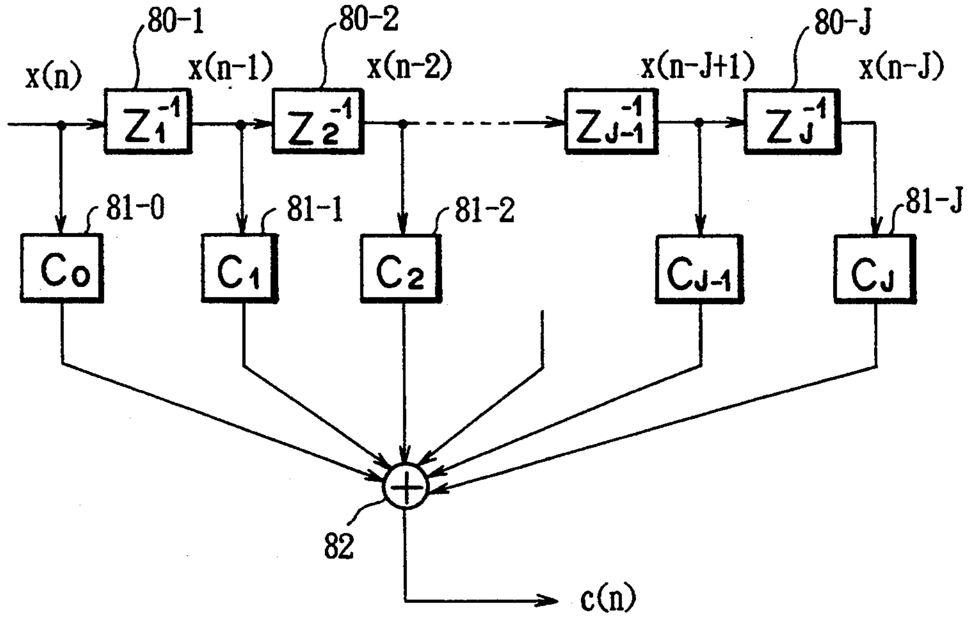
FIG. 11 PRIOR ART
FIG. 11 is a block diagram showing a somewhat detailed construction of a transfer characteristic compensation section of the noise reducing apparatus of FIG. 9.

The transfer characteristic compensation section 5 will be described in more detail first. The transfer characteristic compensation section 5 may be, constructed from a transfer characteristic compensation section of such a construction of the conventional transfer characteristic compensation section as described hereinabove with reference to FIG. 11, but can be simplified in construction since it receives a pulse signal as an input signal thereto.

In particular, it is only necessary to add coefficients of those delay elements at which an input pulse is present, and if the amplitude x of pulses is normalized with "1", then the equation (1) given hereinabove is rewritten as $$C(n) = \sum_{i=k}^{k-2} C_i \qquad (6)$$

where k is an orderly number of a delay element at which a first input pulse is present.

Meanwhile, the tap values $C_l$ are determined if the locations of the loudspeaker 14 and the microphone 15 and the characteristics of the digital to analog converter 13 and the loudspeaker 14 are given. Accordingly, if the right side of the equation (6) when the first input pulse is present at the tap number k is calculated in advance and the kth tap value $HC_k$ is calculated in accordance with the following equation $$H^{C}k = \langle i = k, k-2 \rangle \sum_{i=k}^{k-2} C_4 \qquad (7)$$

where Ci=0 when $i<0$ and $i>J$, then the addition processing is not required any more.

Figure 2:
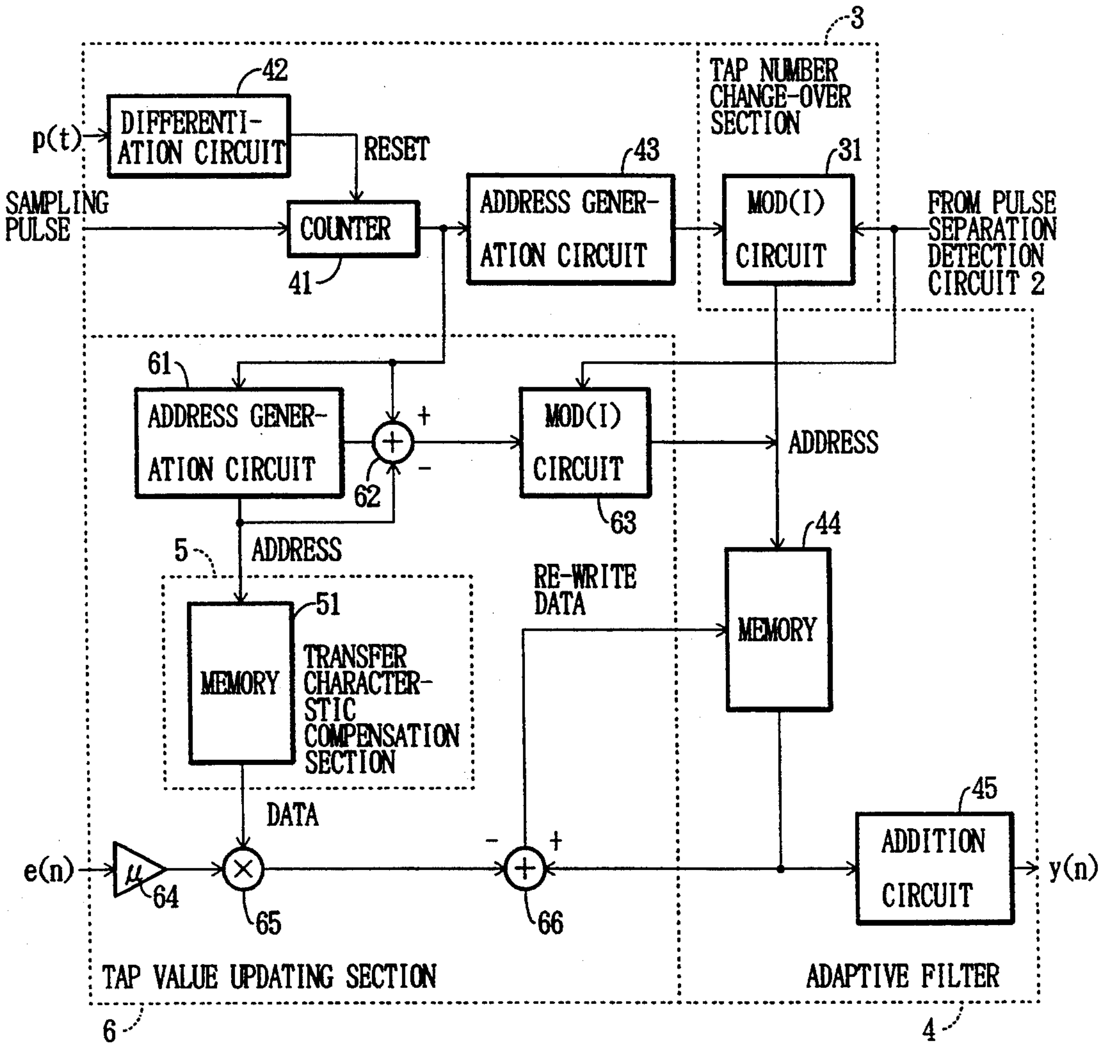
FIG. 2 is a block diagram showing a somewhat detailed construction of a tap change-over section, an adaptive filter, a transfer characteristic compensation section and a tap value updating section of the noise reducing apparatus of FIG. 1.
Figure 3:
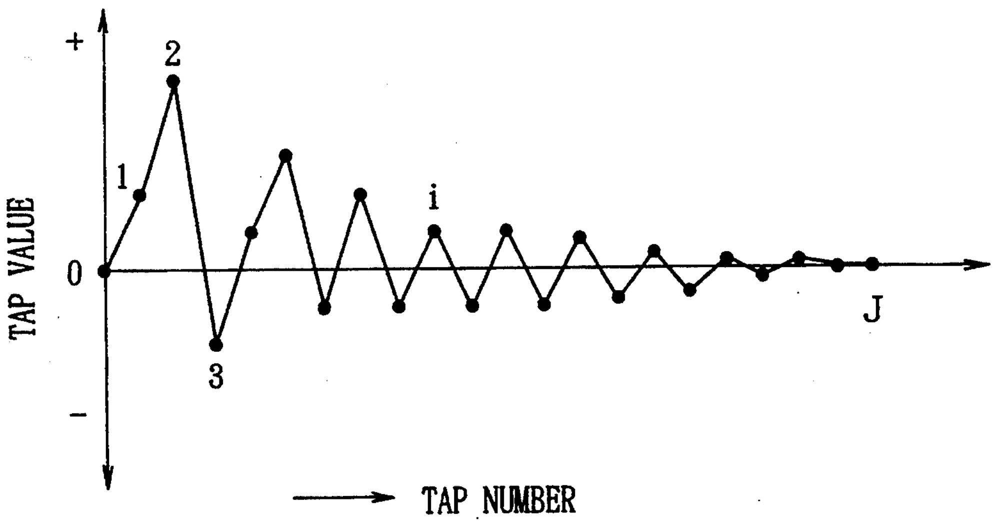
FIG. 3 is a diagram showing exemplary tap values of the transfer characteristic compensation section of FIG. 2.

Referring now to FIG. 2, there is shown a somewhat detailed construction of the tap number changeover section 3, the adaptive filter 4, the transfer characteristic compensation section 5 and the tap value updating section 6.

The transfer characteristic compensation section 5 includes a memory 51 in which tap values $HC_k$ are stored at addresses k each given by the equation (7) above.

The tap number change-over section 3 includes a NOD(I) circuit 31. The tap value updating section 6 includes an address generation circuit 61, a pair of adders 62 and 66, a NOD(I) circuit 63, and a pair of multiplication circuits 64 and 65.

Meanwhile, the adaptive filter 4 includes a counter 41, a differentiation circuit 42, an address generation circuit 54, a memory 44 and an addition circuit 45. The value I to the NOD(I) circuits 31 and 63 is supplied from the pulse interval detection circuit 2.

The counter 41 is reset by a signal obtained by differentiation of a pulse generated from the synchronizing pulse generation circuit 1 by means of the differentiation circuit 42 and repetitively counts between the count values of 0 and I-1.

The address generation circuit 43 generates address values equal to the count value of the counter 41, the count value minus 1 and the count value minus 2 in a time-dividing condition, The three addresses corresponds to for $i=K_1$ to $K_2$ of the equation (5).

The MOD(I) circuit 31 converts a data value generated from the address generation circuit 43 into a value to modulus I and sends out the value as an address of the memory 44. In particular, when I is, for example, 30, the MOD(I) circuit 31 outputs 0 when the data value is 30, outputs 1 when the data value is 31, but outputs 29 reversely when the data value is $-1$, and outputs 28 when the data value is $-2$.

A data value (tap value) at the address is read out from the memory 44 and added at and outputted from the addition circuit 45. In particular, the addition circuit 45 performs addition of the equation (5) and outputs y(n).

Figure 10:
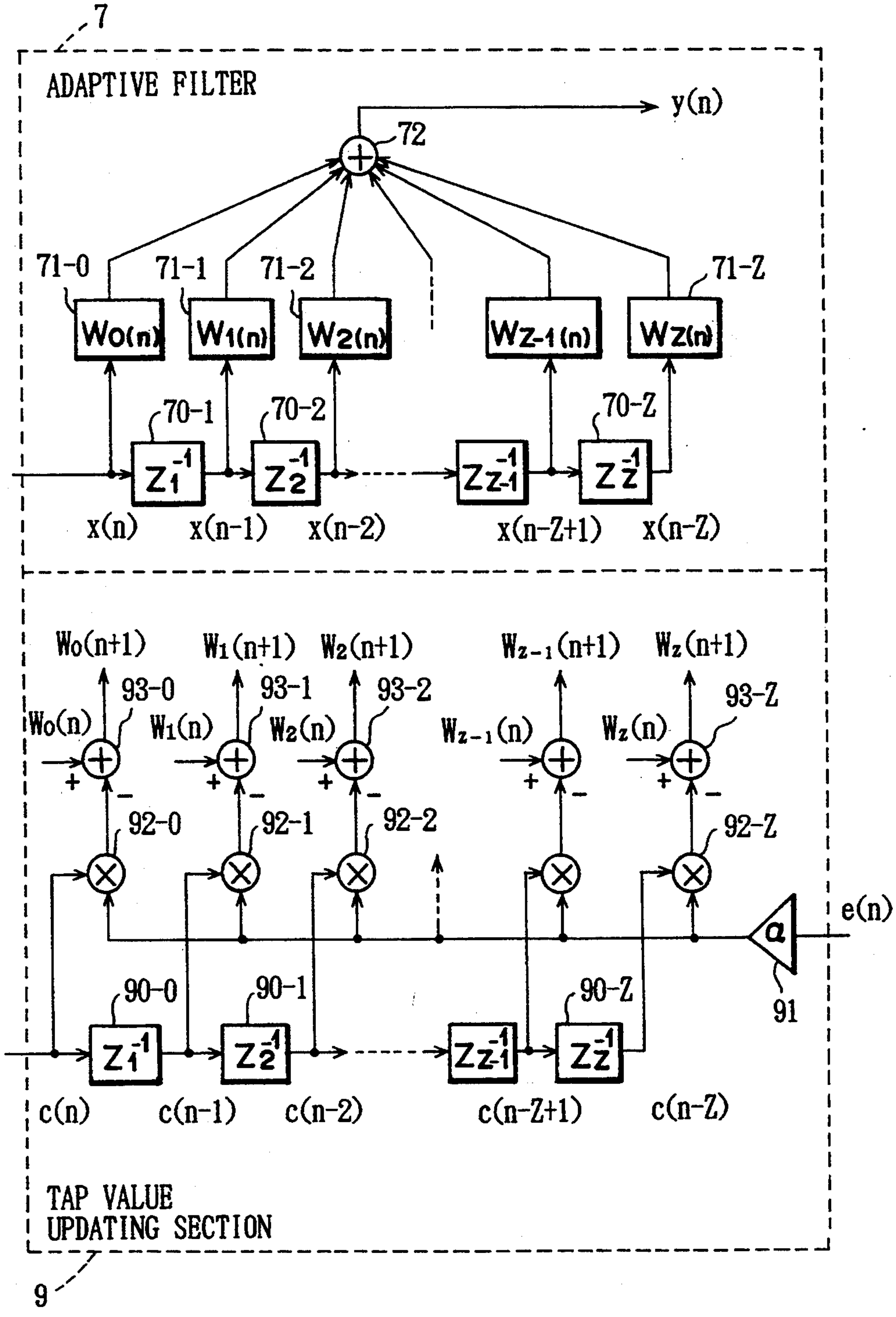
FIG. 10 PRIOR ART
FIG. 10 is a block diagram showing a somewhat detailed construction of an adaptive filter and a tap value updating section of the noise reducing apparatus of FIG. 9.

Calculation of the output value y(n) at the adaptive filter 4 will be described in more detail in contrast with calculation by the construction of the conventional adaptive filter shown in FIG. 10. In particular, a synchronizing pulse p(t) is inputted from the synchronizing pulse generation circuit 1 and propagates through the delay elements 70.

Figure 4:
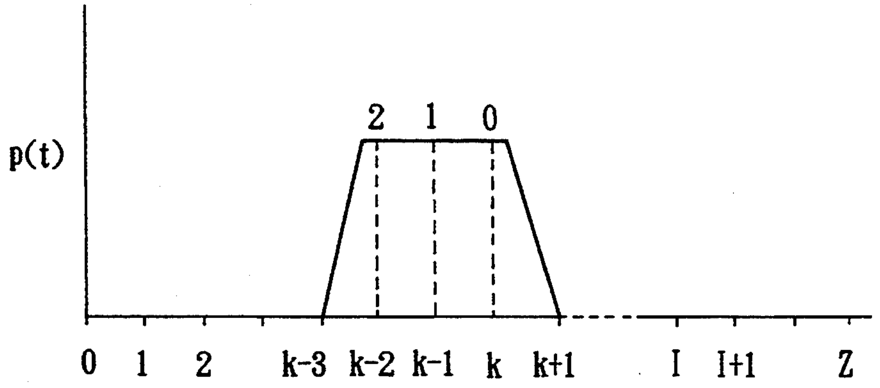
FIG. 4 is a diagram showing a synchronizing pulse on a delay element.

FIG. 4 shows the synchronizing pulse p(t) in a condition wherein it propagates through the delay elements 70. In FIG. 4, the abscissa indicates the number of elements. Further, as assumed hereinabove, the synchronizing pulse p(t) has a width of three sampling pulses.

The count value of the counter 41 shown in FIG. 2 corresponds to the element number k at which the synchronizing pulse p(t) shown in FIG. 4 is present. In this instance, the address generation circuit 43 generates, based on k, addresses k, k-1 and k-2.

Figure 8:
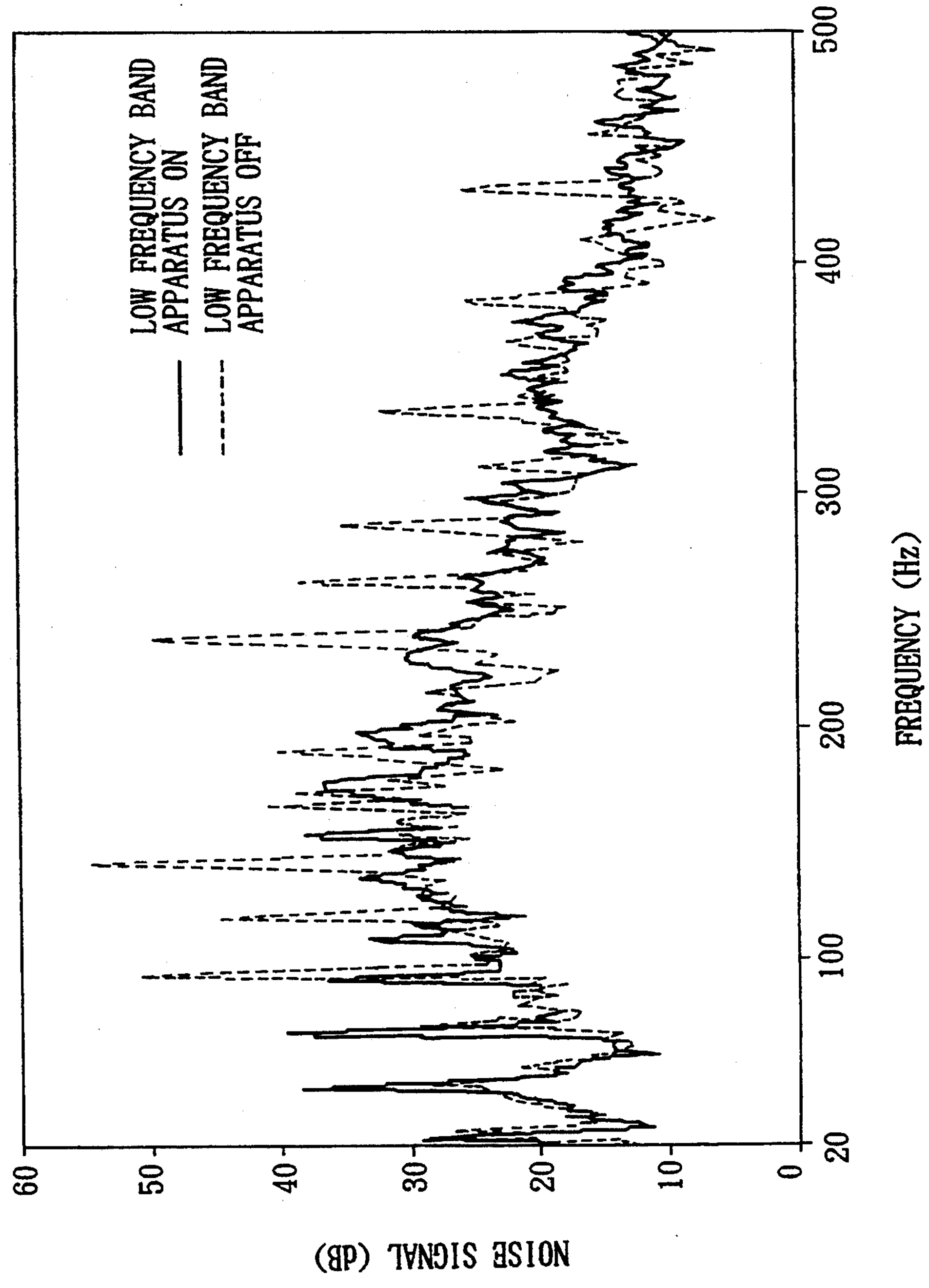
FIG. 8 is a diagram showing the noise reducing characteristic of the noise reducing apparatus of FIG. 7 when two different frequency band loudspeakers are employed.
Figure 9:
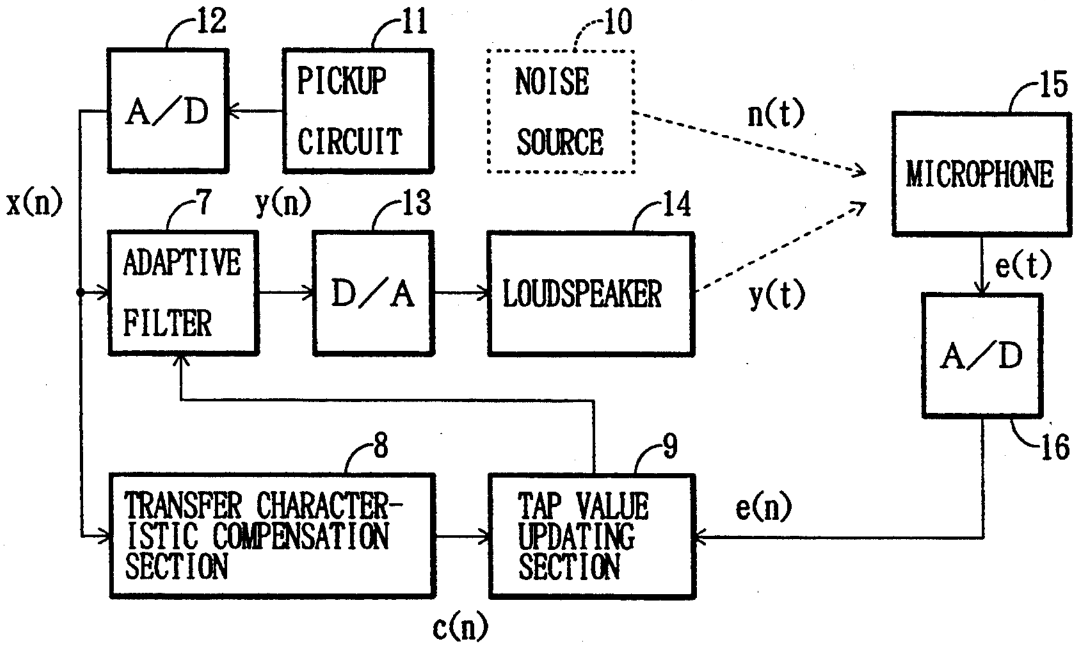
F I G. 9 PRIOR ART
FIG. 9 is a block diagram showing a general construction of a conventional noise reducing apparatus.

Accordingly, the output value y(n) outputted from the addition circuit 45 is obtained by, as seen from FIG. 5, closing $W_Z$ at $W_I$ from the tap value $W_0$ of the adaptive filter shown in FIG. 8 and performing a same multiplication as addition of the tap values from $W_k$ to $W_{k-2}$.

After the calculation of y(n) at the addition circuit 45 is completed, updating of the tap value stored in the tap value memory 44 is started.

When the count value outputted from the counter 41 varies, the address generation circuit 61 generates address signals from 0 to J corresponding to k given by the equation (7) above in a time-dividing condition.

A transfer characteristic $HC_k$ is read out from the memory 51 using the address signal generated from the address generation circuit 61 as an address and inputted to the multiplier 65, from which a calculation output of $\beta.e(n).HC_k$ is obtained, where $\beta=\alpha x$ a, and a is a maximum value of pulses.

Meanwhile, the address signal generated from the address generation circuit 61 is subtracted from the count value of the counter 41 and then inputted to the MOD(I) circuit 63.

The output of the MOD(I) circuit 63 is supplied as an address to the memory 44 In which the tap values are stored so that a tap value $W_k$ (n) is read out from the memory 44 and inputted to the addition circuit 66.

The addition circuit 66 subtracts the output of the multiplication circuit 65 from the tap value $W_k$ (n) to obtain a tap value $W_k$ (n+1) given by $$W_i(n+1)-W_i(n)-\beta.e(n).HC_{k-i} \quad \ldots (9)$$

and the tap value $W_k$ (n+1) is stored into the address k of the memory 44 to update the tap value.

Since the addresses of 0 to J are generated from the address generation circuit 61, where the count value of the counter 41 is k, the data at the addresses of the memory 44 corresponding to k to k-J are updated. In other words, updating of the taps $W_k$ to $W_{k-J}$ of the conventional adaptive filter of FIG. 8 is performed as seen in FIG. 6.

It is to be noted that, while the noise reducing apparatus of the embodiment is described including a single loudspeaker and a single microphone, the present invention can be applied also to a noise reducing apparatus which includes a plurality of loudspeakers and/or microphones.

Figure 7:
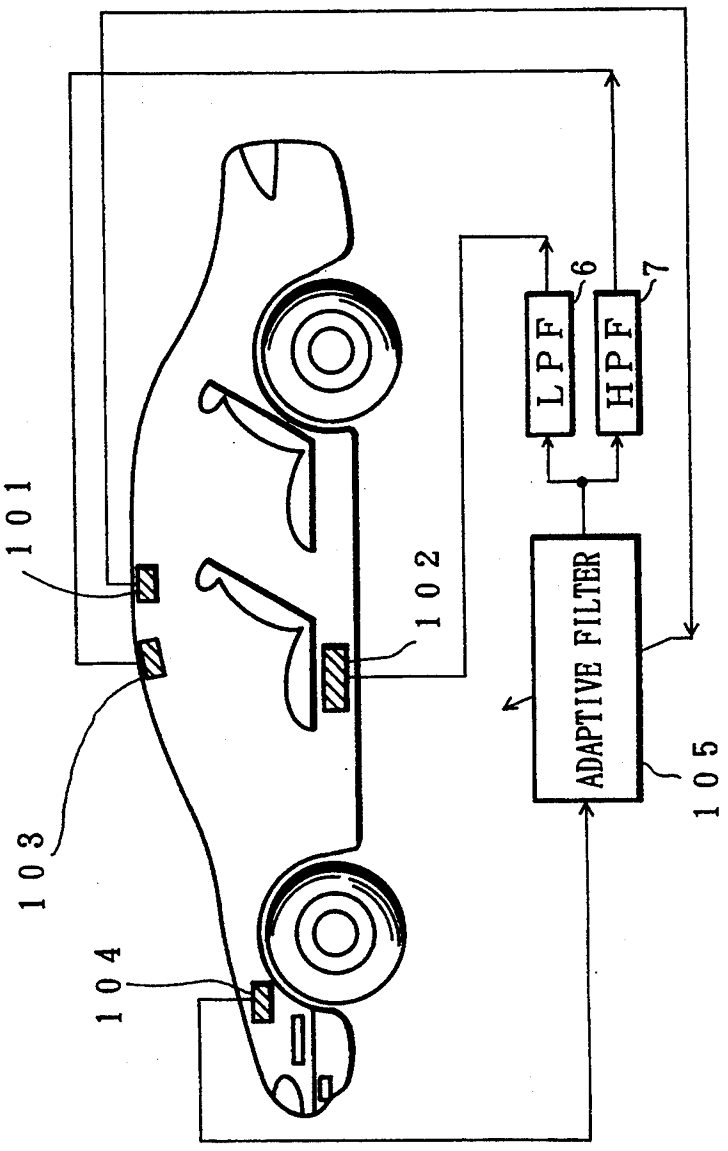
FIG. 7 is a schematic diagrammatic view of a noise reducing apparatus for a room of an automobile to which the present invention is applied.

Referring now to FIG. 7, there is shown a noise reducing apparatus for a room of an automobile to which the present invention is applied. The noise reducing apparatus shown includes a microphone 101, an adaptive filter 105 and a noise pickup 104 similar to those of the conventional noise reducing apparatus described hereinabove with reference to FIG. 12.

The noise reducing apparatus further includes a low frequency band loudspeaker 102 for converting an electric signal of a low frequency band into sound waves, a high frequency band loudspeaker 103 for converting an electric signal of a high frequency band into sound waves, a low-pass filter (LPF) 106 and a high-pass filter (HPF) 107.

The microphone 101 is installed on the ceiling near the ears of a driver and/or a passenger or passengers above a seat of an automobile. Further, the low frequency band loudspeaker 102 is installed below the seat since it is large in size. Meanwhile, the high frequency band loudspeaker 103 is small in size and installed on the ceiling in the proximity of the microphone 101 above the seat.

Where the microphone 101, the low frequency band loudspeaker 102 and the high frequency band loudspeaker 103 are located in such a manner as described above, the distance between the high frequency band loudspeaker 103 and the microphone 101 is so short that main waves of high frequency waves are much greater than reflection waves of the high frequency waves, and consequently, the fluctuation of the transfer characteristic is eliminated and noise of a high frequency band can be reduced efficiently.

Figure 13:
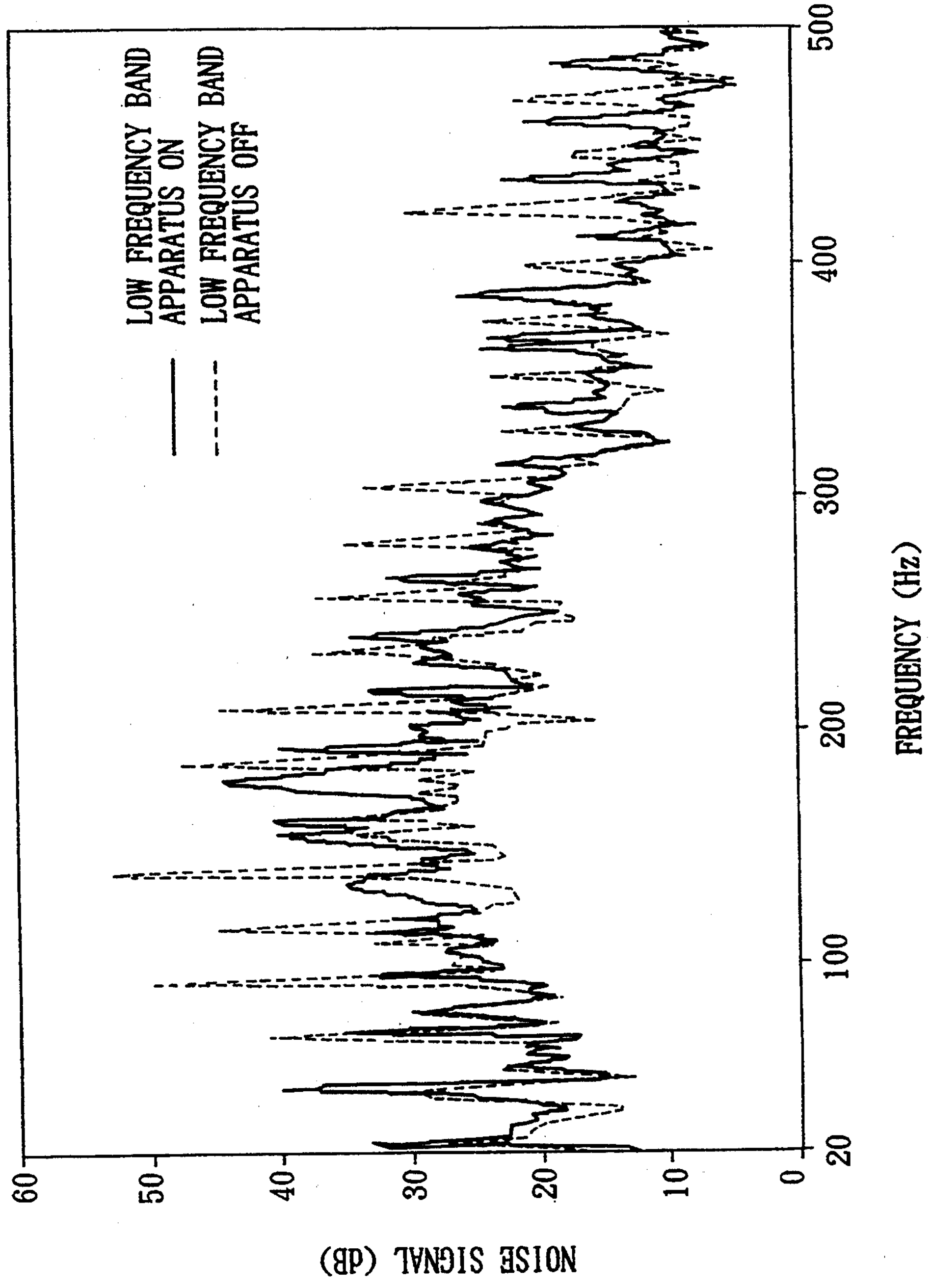
FIG. 13 PRIOR ART
FIG. 13 is a diagram showing the noise reducing characteristic of the noise reducing apparatus of FIG. 12.

FIG. 8 shows an exemplary noise reducing characteristic of the noise reducing apparatus for a room of an automobile described above where the microphone is installed on the ceiling above the seat and the low frequency band loudspeaker is installed below the seat while the high frequency band loudspeaker is installed on the ceiling above the seat. From comparison with FIG. 13, it can be seen that the noise reducing effect in a high frequency band is significantly high.

Figure 12:
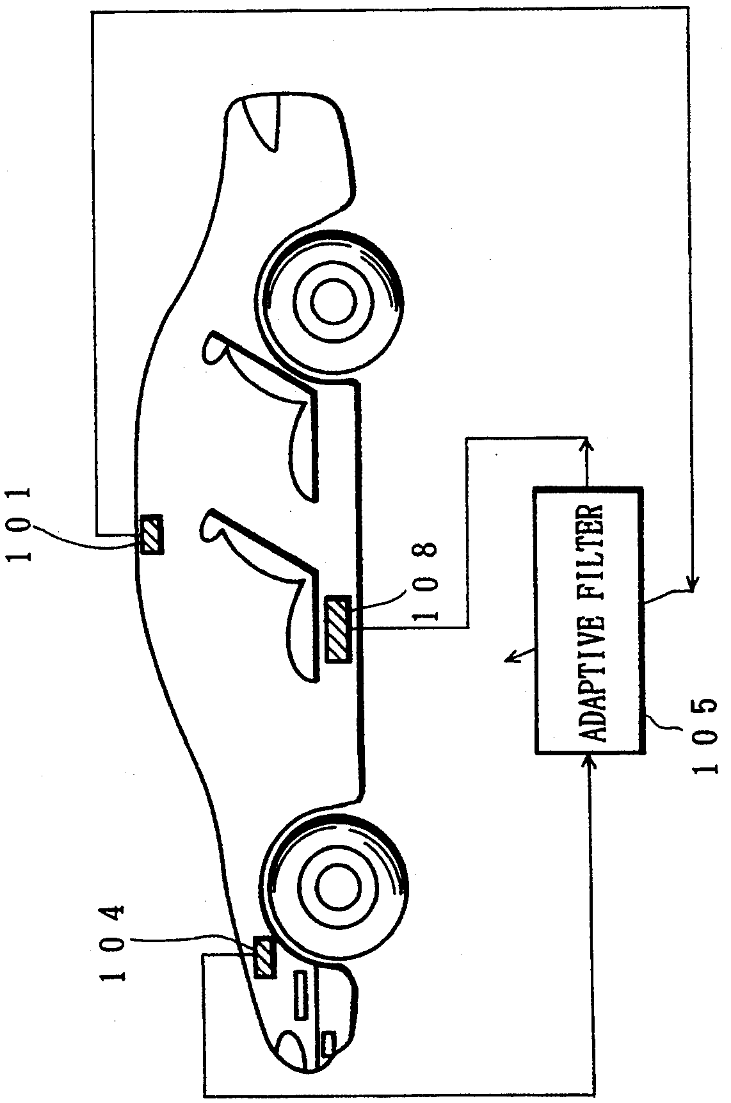
FIG. 12 PRIOR ART
FIG. 12 is a schematic diagrammatic view of a conventional noise reducing apparatus for a room of an automobile.

It is to be noted that operation of the adaptive filter 105 is the same as that described hereinabove in connection with the conventional noise reducing apparatus with reference to FIG. 12 and overlapping description thereof is omitted herein to avoid redundancy.

It is to be noted that, while, in the embodiment described above, the microphone is located on the ceiling above the seat and the low frequency band loudspeaker is installed below the seat while the high frequency band loudspeaker is installed on the ceiling above the seat, either one of the microphone and the high frequency band loudspeaker may alternatively be installed on a side face of a seat back of the seat or some other location.

Further, while the low frequency band loudspeaker in the embodiment described above is installed below the seat, a loudspeaker of a car radio not shown installed in the room of the automobile may be used commonly as the low frequency band loudspeaker.

Having now fully described the invention, it will be apparent to one of ordinary skill in the art that many changes and modifications can be made thereto without departing from the spirit and scope of the invention as set forth herein.

What is claimed is:

1. A noise reducing apparatus, comprising:

a microphone;

an adaptive filter for generating a signal to reduce noise inputted to said microphone according to a transfer characteristic and to an output signal of said microphone;

transfer characteristic compensation means for compensating the transfer characteristic when said microphone outputs the output signal;

a synchronizing pulse generation circuit for generating a pulse signal synchronized with the period of the noise;

a pulse interval detection circuit for detecting the interval between pulses of the pulse signal generated from said synchronizing pulse generation circuit;

tap number change-over means for changing over the number of taps of said adaptive filter to a number with which the delay amount of a tapped delay line of said adaptive filter is equal to the interval detected by said pulse interval detection circuit; and a loudspeaker for generating sounds in response to the signal from said adaptive filter.

2. A noise reducing apparatus as claimed in claim 1, wherein said transfer characteristic compensation means includes a non-volatile memory in which tap values are stored in advance and generates a signal for compensation for the transfer characteristic in synchronism with the pulse signal from said synchronizing pulse generation circuit.

3. A noise reducing apparatus as claimed in claim 2, further comprising updating means for updating a number of those tap values of said adaptive filter corresponding to the number of addresses of said memory in which data values for compensation for the transfer characteristic are stored.

* * * * *